United States Patent
Tsutsui et al.

(10) Patent No.: US 9,261,421 B2
(45) Date of Patent: Feb. 16, 2016

(54) APPARATUS AND METHOD FOR MEASURING FIXING FORCE

(71) Applicant: Mitsubishi Hitachi Power Systems, Ltd., Nishi-ku (JP)

(72) Inventors: Yoshitaka Tsutsui, Tokyo (JP); Nobuaki Nakasu, Tokyo (JP); Keiji Suzuki, Tokyo (JP); Kengo Iwashige, Tokyo (JP); Mitsuru Onoda, Tokyo (JP); Harumasa Tsuchiya, Tokyo (JP); Yasuaki Kageyama, Tokyo (JP)

(73) Assignee: Mitsubishi Hitachi Power Systems, Ltd., Yokohama (JP)

( * ) Notice: Subject to any disclaimer, the term of this patent is extended or adjusted under 35 U.S.C. 154(b) by 73 days.

(21) Appl. No.: 14/102,082

(22) Filed: Dec. 10, 2013

(65) Prior Publication Data
US 2014/0260526 A1    Sep. 18, 2014

(30) Foreign Application Priority Data
Mar. 15, 2013  (JP) .................. 2013-052636

(51) Int. Cl.
G01M 7/00 (2006.01)
G01N 3/30 (2006.01)
G01N 3/32 (2006.01)
G01P 15/00 (2006.01)
G01L 5/00 (2006.01)

(52) U.S. Cl.
CPC ............ G01L 5/0028 (2013.01); G01L 5/0038 (2013.01); *G01N 3/30* (2013.01)

(58) Field of Classification Search
CPC .... G01M 7/08; G01N 29/045; H02K 15/0018

USPC .......... 73/572, 582, 588, 645, 12.01, 581
See application file for complete search history.

(56) References Cited

U.S. PATENT DOCUMENTS

| 4,901,572 A | * | 2/1990 | Suyama ........................ 73/572 |
| 5,295,388 A | * | 3/1994 | Fischer et al. ............. 73/12.09 |
| 6,631,335 B2 | * | 10/2003 | Lusted et al. ................. 702/56 |

FOREIGN PATENT DOCUMENTS

| JP | 2000146929 A | * | 5/2000 | ............ G01N 29/12 |
| JP | 3973203 B2 | | 9/2007 | |
| JP | 4456723 B2 | | 4/2010 | |

OTHER PUBLICATIONS

Machine Translation of Title and Abstract for Jp 2000-146929 A, Date of patent doc.: May 26, 2000, Publisher: Japan Platform for Patent Information, National Center for Inductrial Property Information and Training, pp. 1; translation obtained: Jul. 26, 2015.*

* cited by examiner

*Primary Examiner* — Lisa Caputo
*Assistant Examiner* — Roger Hernandez-Prewitt
(74) *Attorney, Agent, or Firm* — Crowell & Moring LLP

(57) ABSTRACT

A fixing force measuring apparatus including a section for applying a predetermined controlled hammering force to a wedge surface to generate a hammering sound, a section for controlling the hammering sound generated, a section for obtaining plural kinds of feature quantities such as a feature quantity due to a hammering sound energy, and a feature quantity due to a frequency of the hammering sound from the hammering sound collected by an arithmetic operation, and a section for obtaining a fixing force corresponding to the plural kinds of feature quantities by using a correlative relationship between the wedge fixing force previously obtained, and the plural kinds of feature quantities.

12 Claims, 12 Drawing Sheets

(CROSS-SECTIONAL VIEW TAKEN ON LINE E - E)

RELATION BETWEEN CENTER-OF-GRAVITY FREQUENCY DISPERSION AND FIXING FORCE

APPARATUS AND METHOD FOR MEASURING FIXING FORCE

INCORPORATION BY REFERENCE

The present application claims priority from Japanese patent application JP-2013-052636 filed on Mar. 15, 2013, the contents of which are hereby incorporated by reference into this application.

BACKGROUND OF THE INVENTION

The present invention relates to an apparatus and a method for measuring fixing forces for fixing states of various members in an electric machine.

A generator as one of measurement objects includes a rotor and a stator. A change in a magnetic field generated by rotation of the rotor is converted into an electric energy by the stator. The stator has a structure in which a coil is inserted into a slot of a core formed by laminating silicon steel plates one upon another, and fixing is carried out under a pressure by an insulating member.

For a fixing method under a pressure, a structure is adopted in which a corrugated plate spring and a wedge as a plate-like member are stacked on top of each other above a coil, and the corrugated plate spring is pinned down by the wedge while the corrugated plate spring is compressed, thereby fixing a coil conductor.

In such a fixing structure, it is necessary to maintain and manage the coil in a predetermined fixing state under a pressure. In the generator having the coil fixing structure described above, after a lapse of predetermined time (usage period), the wedge is inspected for the fixing state thereof. Also, if there is the loose in the fixing state of the wedge, then, for recovery of an applied pressure, replacement, adjustment, and maintenance of the wave-like spring and the wedge are carried out. Until now, the inspection and judgment for the fixing state of the coil has relied on an organoleptic examination in which the fixing state of the coil is judged based on sounds and vibrations. In this case, a person strikes the wedge with a hammer for examination, thereby generating the sounds and vibrations.

A method described in Japanese Patent No. 3 973 203 is known as an attempt to quantify the organoleptic examination. With this method, a member is excited, and a vibration response is detected and is compared with plural vibration responses previously recorded, thereby estimating a pressure applied to a wedge. Also, this method includes a step of obtaining a center of an energy band of spectra as a spectral analysis for the comparison with the vibration response. In addition, Japanese Patent No. 4 456 723 describes a method of quantitatively judging a degree of soundness of concrete based on a hammering sound from the concrete. This method is such that a surface of the concrete is hit by an impulse hammer, and a known quantity of hammering input and a hammering sound propagated through the concrete are both analyzed, thereby judging the degree of soundness of the concrete.

SUMMARY OF THE INVENTION

When the fixing force of the wedge is judged by a person, the dispersion is caused in the judgment results due to a level of skill, a sensation, a physical condition, and the like of an individual measurer.

In addition, the report by Japanese Patent No. 3 973 203 shows that the frequency exhibiting the center of the energy band of the spectra of the hammering sound has a connection with the loose state of the wedge. However, since the hammering sound frequency is changed due to the hammering position, the hitting force (hammering force) or the like, the sufficient precision is not obtained in terms of the quantitative value of the wedge fixing force only by the method described in Japanese Patent No. 3973203.

In addition, Japanese Patent No. 4456723 shows the method in which the surface of the concrete is struck with the impulse hammer, and then the degree of the soundness of the concrete is obtained in the form of a ratio of the hammering input measured with the impulse hammer to an amplitude of the generated hammering sound. This method is easy to utilize in the case of a large physical object like a concrete structural object because a hammering position and a sound collecting position can be both freely selected. However, in the evaluation of the fixing force of the wedge of the generator, the surface of the relatively small plate-like object must be struck. Therefore, this method is difficult to apply to the evaluation of the fixing force of the wedge of the generator. In addition, the wedge has an elongated plate-like shape, and in the method described in Japanese Patent No. 4456723, the hammering position and the hammering sound collecting position are different from each other. Therefore, since a correlative relationship between the impulse hammer output in the hammering position and the amplitude of the vibration of the hammering sound is weak, and thus it is impossible to obtain the sufficient precision of the estimation of the fixing force.

The present invention provides plural solutions for the problems described above. As giving an example thereof, there is provided an apparatus for measuring a fixing force, including a section for applying a predetermined controlled hitting force to a surface of a wedge, thereby generating a hitting sound; a section for collecting the hitting sound generated; a section for obtaining plural kinds of feature quantities such as a feature quantity due to a hitting sound energy, and a feature quantity due to a frequency of the hitting sound from the hitting sound collected through an arithmetic operation; and a section for obtaining the fixing force corresponding to the plural kinds of feature quantities by using a correlative relationship between a wedge fixing force previously obtained, and the plural kinds of feature quantities.

As set forth hereinabove, according to the present invention, since the highly precise quantification of the fixing forces of the wedge of the generator stator becomes possible, it is possible to enhance the reliability of the wedge incorporating work in the assembly of the generator stator. In addition, in the generator being used, the wedge fixing force is periodically measured in the periodic examination or the like, which leads to that the temporal change of the wedge fixing force (coil fixing force) can be grasped. Accumulating the data on the temporal change of the wedge fixing force makes it possible to estimate the time for replacement of the stator wedge. As a result, since the maintenance of the generator can be efficiently carried out, it is possible to reduce the cost, the energy, and the like which are involved with the maintenance.

Other objects, features and advantages of the invention will become apparent from the following description of the embodiments of the invention taken in conjunction with the accompanying drawings.

DESCRIPTION OF THE EMBODIMENTS

Hereinafter, embodiments of the present invention will be described in detail with reference to the accompanying drawings.

First Embodiment

Figure 2:
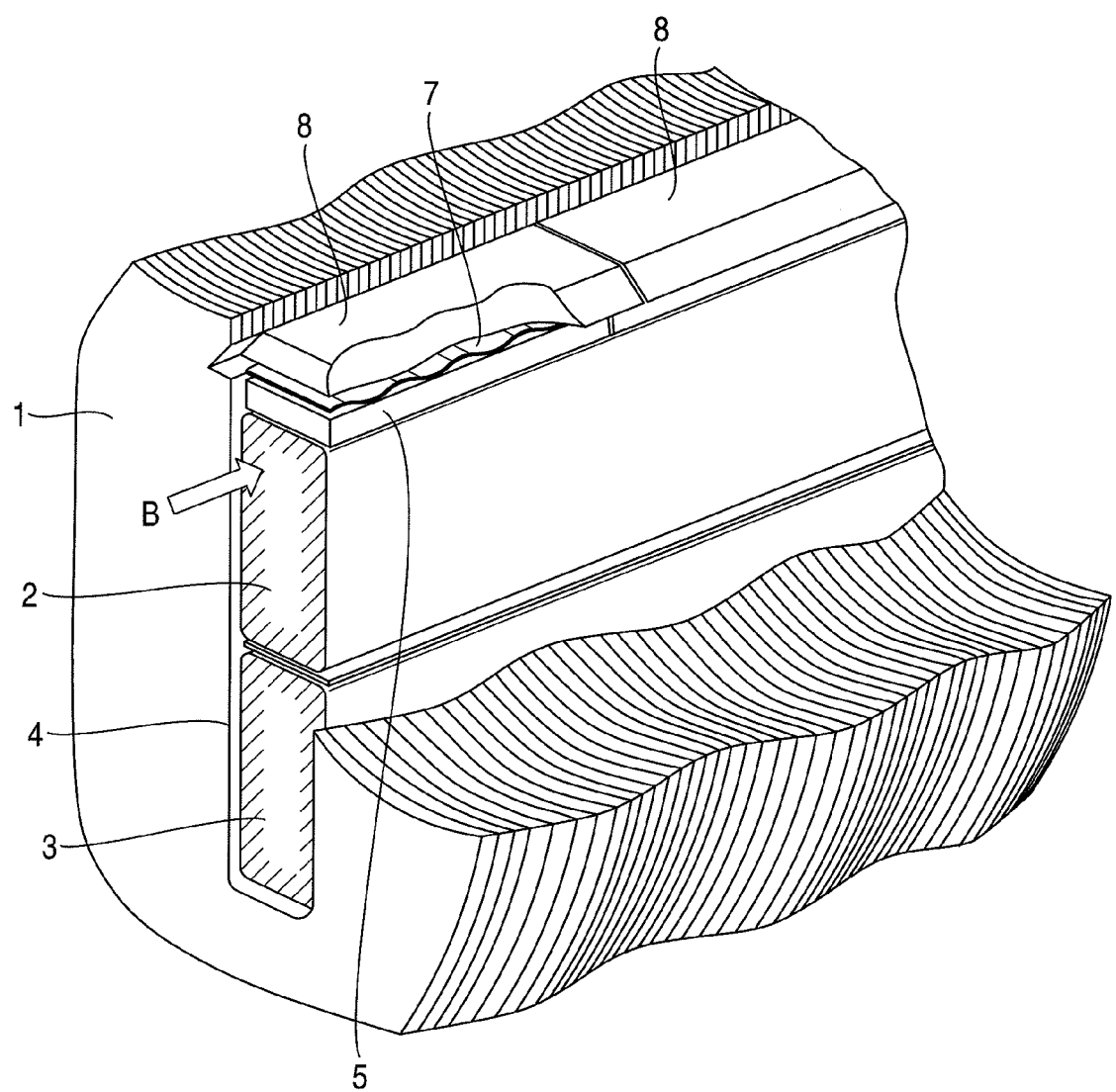
FIG. 2 is a partial cross-sectional view showing a structure of a generator stator as a measurement object product.
Figure 3:
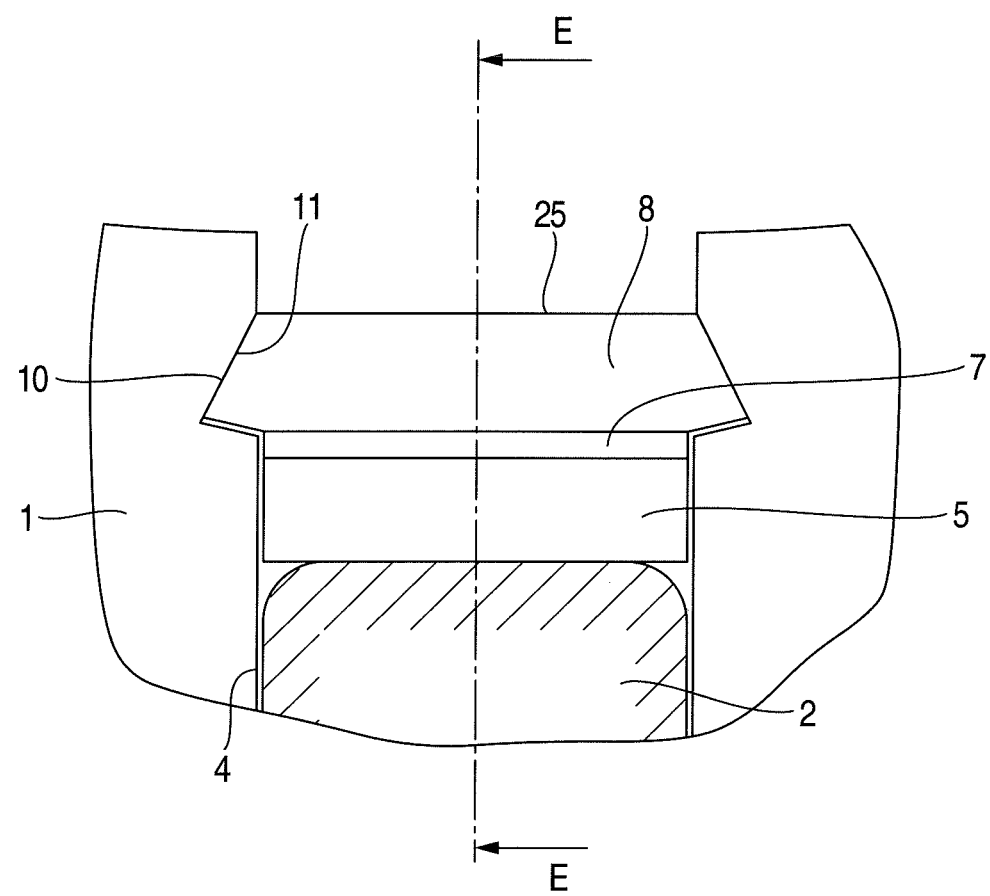
FIG. 3 is a partially enlarged view of FIG. 2.

Firstly, a description will now be given with respect to a structure of an example of a measurement object with reference to FIGS. 2 and 3. FIG. 2 is a partial cross-sectional view showing a part of a generator stator. FIG. 3 is a view on an arrow B of FIG. 2.

The generator stator has a coil fixing structure, as shown in FIGS. 2 and 3, in order to prevent a coil from being vibrated by an electromagnetic force which is generated in the coil by a current in a phase of power generation. In FIG. 2, reference numeral 1 designates a core which is formed by laminating silicon steel plates one upon another, reference numeral 4 designates a groove provided in the core, and reference numerals 2 and 3 respectively designate coils which are both inserted into the groove 4. A plate 5, a corrugated plate spring 7, and a wedge 8 are laminated in this order on the coil 2. Materials of the plate 5, the corrugated plate spring 7, and the wedge 8 are each a composite material. In this case, the composite material is formed in such a way that a suitable material is impregnated with a resin having a high insulating property.

In FIG. 3, the wedge 8 is inserted so as to be fitted into both a cutout groove 10 formed in the groove 4 of the core 1, and a tapered portion 11 of the wedge 8. In this structure, the corrugated plate spring 7 is held in a compression state. Both the coils 2, 3 are pressed by a force (i.e., a reaction force) which is generated by the corrugated plate spring 7 thus compressed. In this case, this reaction force is applied to the wedge 8, and the reaction force applied to the wedge 8 is received by the cutout grooves 10, of the groove 4, which is provided in the core 1 and into which the wedge 8 is fitted. Since in such a coil fixing structure, it is difficult to directly measure the fixing states of the coils 2, 3, the fixing state of the wedge 8 to which the identical reaction force is applied is measured.

Next, a description will be given with respect to a wedge fixing force measuring apparatus shown in FIG. 1.

Figure 1:
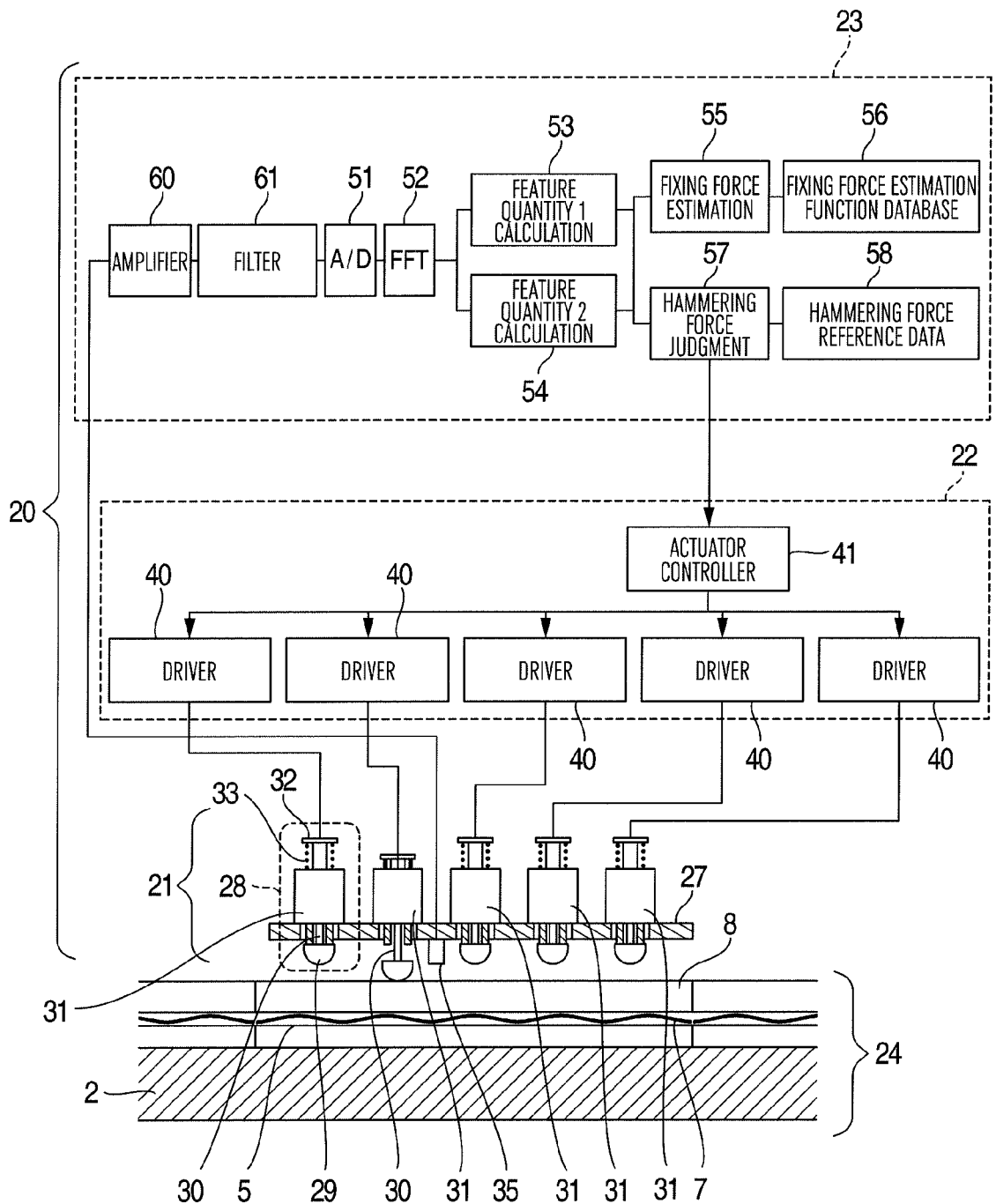
FIG. 1 is a block diagram, partly in view, showing a configuration and a structure of a wedge fixing force measuring apparatus according to a first embodiment of the present invention.

In FIG. 1, reference numeral 20 designates the wedge fixing force measuring apparatus. The wedge fixing force measuring apparatus 20 is roughly divided in structure into three units. Reference numeral 21 designates a hammering unit, and reference numeral 22 designates a hammering control unit for controlling and driving the hammering unit 21. Also, reference numeral 23 designates a hammering sound processing unit for processing a hammering sound generated by the hammering unit 21.

In FIG. 1, reference numeral 24 designates a cross-sectional view taken on line E-E of FIG. 3.

In the hammering unit 21, five hammering mechanisms 28, for example, are disposed in a base 27. In the hammering mechanism 28, reference numeral 29 designates a hammer for hammering the wedge 8. The hammer 29 is fixed to a shaft 30. One end of the shaft 30 has such a structure as to be fitted into a solenoid actuator 31. A guard 32 is fixed to the other end of the shaft 30. A coil spring 33 is inserted into a space defined between the guard 32 and the solenoid actuator 31. The solenoid actuator 31 is connected to the hammering control unit 22 and controls the driving for a vertical operation of the hammer 29. A microphone 35 for collecting a hammering sound is fixed to the hammering unit 21. Also, an output terminal of the microphone 35 is connected to the hammering sound processing unit 23.

To individually drive, for example, the five solenoid actuators 31, the hammering control unit 22 is composed of five sets of drivers 40, and an actuator controller 41 for controlling the five sets of drivers 40.

A duty ratio of a drive current pulse is controlled by, for example, using a Pulse Width Modulation (PWM) system for a current applied to the solenoid actuator 31, thereby making it possible to adjust the control for the hammering force of the hammering mechanism 28 by the hammering control unit 22.

The hammering sound processing unit 23 is composed of an amplifier 60, a filter 61, an A/D (Analog/Digital) converter 51, a Fast Fourier Transform (FFT) processor 52, a feature quantity 1 computer 53, and a feature quantity 2 computer 54. In addition thereto, the hammering sound processing unit 23 is composed of a fixing force estimator 55, a fixing force estimation function database 56, a hammering force judging unit 57, and hammering force reference data 58. Both the amplifier 60 and the filter 61 adjust an input of an analog signal sent from the microphone 35. The A/D converter 51 converts the analog signal sent from the filter 61 into a digital signal. The FFT processor 52 obtains a power spectrum of an output from the digital signal from the A/D converter 51. Both the feature quantity 1 computer 53 and the feature quantity 2 computer 54 carry out an arithmetic operation for obtaining the feature quantities such as a center-of-gravity frequency and a hammering sound energy which will be described later from the power spectrum. The fixing force estimation function database 56 is obtained in the form of a database every object model with a relationship between two kinds of feature quantities obtained from both the feature quantity 1 computer 53 and the feature quantity 2 computer 54, and the fixing force as a function. In this case, the feature quantity 1 computer 53 and the feature quantity 2 computer 54 are different from each other every model of a product.

The fixing force estimator 55 compares the results from both the feature quantity 1 computer 53 and the feature quantity 2 computer 54 with the data in the fixing force estimation function database 56 previously prepared, thereby estimating the fixing force. The wedge fixing force measuring apparatus 20 which is held in a normal state strikes a reference member for hammering sound calibration which is specially prepared, and the results from the feature quantity 1 computer 53 and the feature quantity 2 computer 54 are recorded as the hammering force reference data 58.

Both the hammering force judging unit 57 and the hammering force reference data 58 may be used as may be necessary. The wedge fixing force measuring apparatus 20 strikes a reference member 150 for hammering sound calibration which will be described later as may be necessary to obtain the feature quantities. Then, the hammering force judging unit 57 compares the feature quantities with the hammering force reference data 58, thereby judging the state of the hammering unit 21. When it is judged that the hammering force deviates from a tolerance level, the driving conditions for the solenoid actuator 31 are changed by controlling the duty ratio of the drive current in the PWM control, thereby adjusting the current hammering force to a predetermined hammering force.

The hammering sound processing unit 23 is provided with a signal interface with the hammering controller 22, a control function, an arithmetically operating portion which carries out various arithmetic operations in accordance with computation expressions which will be described later, a recording portion, a display portion, and the like.

Next, a description will be given with respect to a wedge fixing force measuring method using the wedge fixing measuring apparatus 20. Firstly, the hammering unit 21 strikes the wedge 8 as an evaluation object. A hammering start signal is applied to the actuator controller 41 through a switch or the like (not shown). When the actuator controller 41 sends a PWM control signal to the driver 40, and causes the drive current to flow through the solenoid actuator 31, the hammer 29 is descended to hammer the wedge 8. At this time, the coil spring 33 is compressed by the guard 32 at the end of the shaft 30 fixed to the hammer 29. When causing the current to flow through the solenoid actuator 31 is stopped, the hammer 29 is ascended by a force of the compressed coil spring 33. At this time, an applying time of the drive current is several milliseconds, and thus the hammer 29 instantaneously strikes the wedge 8 to generate the hammering sound. In the first embodiment, the hammering action is carried out at intervals of several hundreds of milliseconds from the hammering mechanism 28 on one side in the five hammering mechanisms 28, whereby the hammering sounds are generated in order in the five portions of the wedge 8. The hammering sound generated by the hammering unit 21 is taken in the hammering sound processing unit 23 synchronously with the hammering operation of the hammering unit 21 through the microphone 35. For the synchronization, a solenoid driving timing of the actuator controller 41 of the hammering control unit 22 is used as a trigger.

With regard to a timing of sound recording, the hammering sound is collected synchronously with the hammering timing at a length from several milliseconds before the generation of the hammering sound to about several tens of milliseconds after the generation of the hammering sound. The sound recording start timing and the sound recording time can be changed based on the setting of the conditions within the hammering sound processing unit 23.

Figure 4:
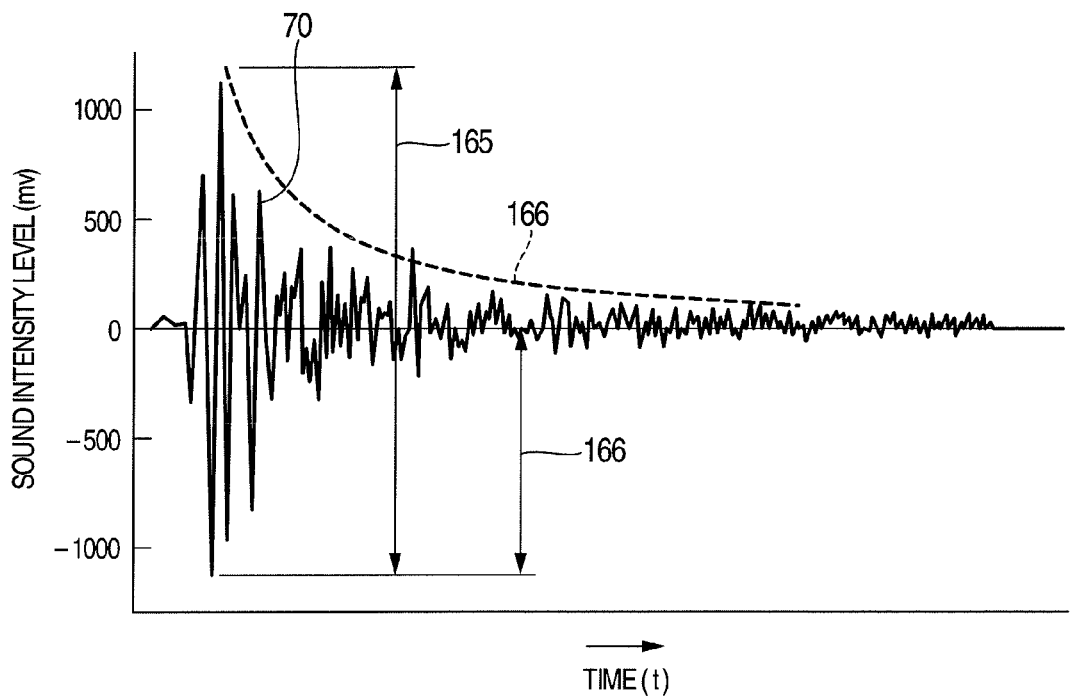
FIG. 4 is a waveform chart showing a hammering sound signal.

After the hammering sound signal taken in the hammering sound processing unit 23 has been adjusted in signal level by the amplifier 60, the resulting analog signal is adjusted to an analog signal in a necessary frequency band by the filter 61. The signal thus adjusted is converted from the analog signal into a digital signal by the A/D converter 51. FIG. 4 shows hammering sound data 70, as a function f(t) of time, which is converted into the digital signal. In FIG. 4, an axis of abscissa represents a time axis, and an axis of ordinate represents a value which is obtained by converting an intensity of the hammering sound signal into a voltage level.

Figure 5:
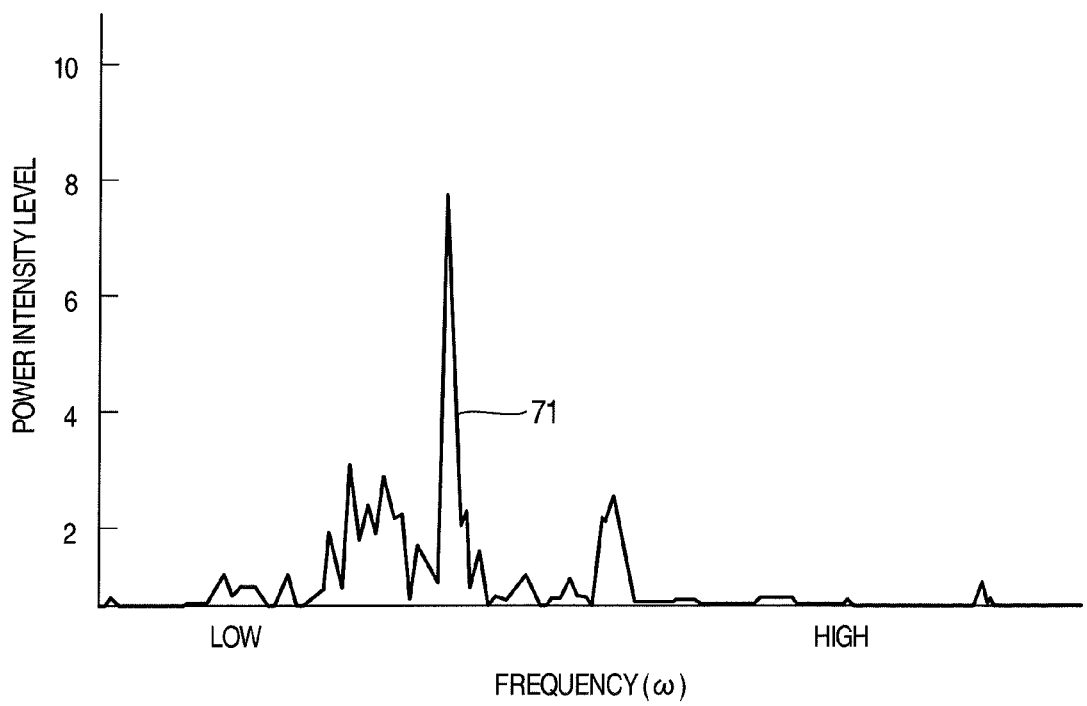
FIG. 5 is a power spectrography of the hammering sound signal.

Next, the hammering sound data obtained through the AD conversion is processed in the FFT processor 52, thereby obtaining a power spectrum 71 as a function $X(\omega)$ of a frequency $\omega$ shown in FIG. 5. In FIG. 5, an axis of abscissa represents a frequency $\omega$, and an axis of ordinate represents a signal intensity. Thus, FIG. 5 represents an intensity distribution of the frequencies contained in the hammering sound.

Next, two kinds of feature quantities are obtained based on Expressions (1) and (2) from the power spectrum 71 by using both the feature quantity 1 computer 53 and the feature quantity 2 computer 54.

A center-of-gravity frequency, $f_g$, is obtained from Expression (1):

$$f_g = \frac{\int (X(\omega) \times \omega) d\omega}{\int X(\omega) d\omega} \quad (1)$$

wherein $\omega$ represents the frequency of the spectrum, $X(\omega)$ represents the signal intensity of the power spectrum.

A hammering sound energy, $E_E$, is obtained from Expression (2):

$$E_E = \int X(\omega) d\omega \quad (2)$$

In the first embodiment, to reduce the dispersion of the hammering sound feature quantities due to the difference of the hammering positions, a value which is obtained by collecting the hammering sounds from five portions of one wedge 8, and averaging the hammering sounds thus collected is used as the feature quantity of the wedge 8.

Figure 6:
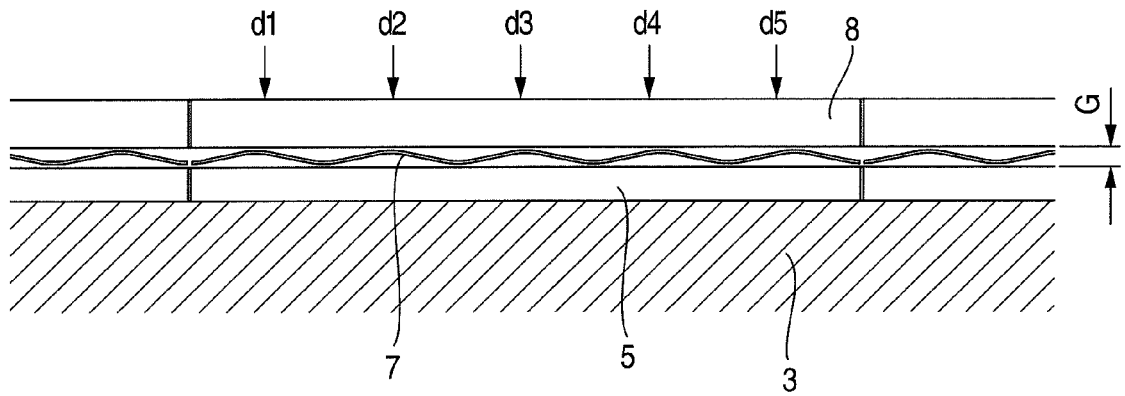
FIG. 6 is an explanatory view of wedge hammering positions.
Figure 7:
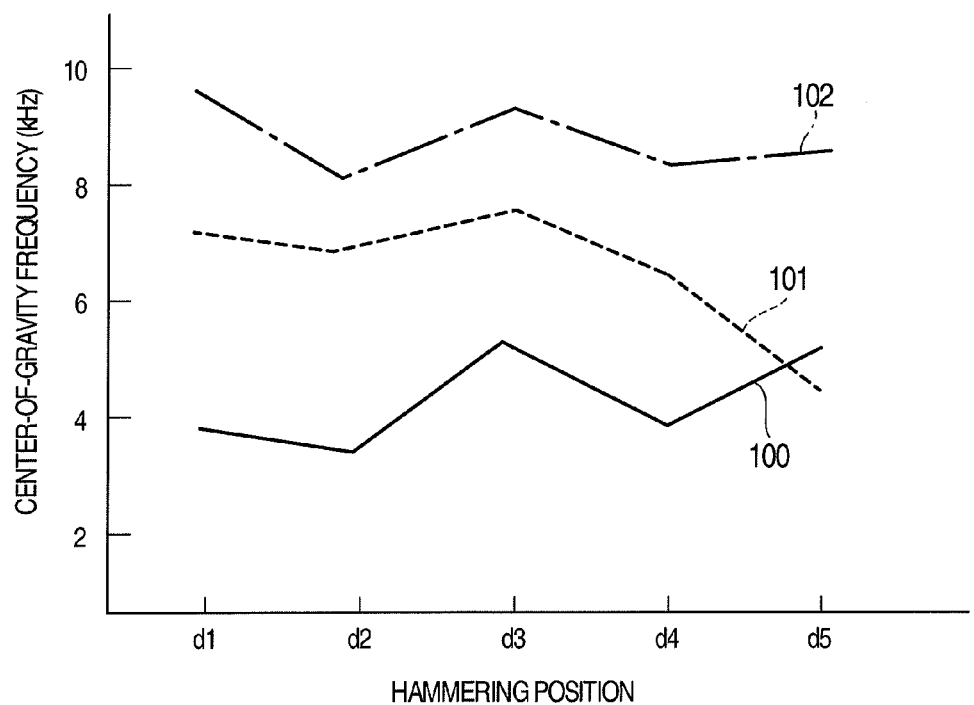
FIG. 7 is a graph representing a relationship between a hammering position and a center-of-gravity frequency.

A description will now be given with respect to an effect of the hammering carried out against plural portions of one wedge. FIG. 6 shows a partial cross-sectional view of the stator core (a cross-sectional view taken on line E-E of FIG. 3). Five portions d1 to d5 of the wedge 8 are struck, for example, at equal pitches. FIG. 7 shows results of obtaining the center-of-gravity frequency from the sounds generated by the hammering action by using Expression (1). In FIG. 7, an axis of abscissa represents a hammering position, and an axis of ordinate represents the value of the center-of-gravity frequency. In addition, three graphs 100, 101, 102 in the figure show results of changing the fixing force of the wedge 8 by three levels. The graph 100 shows the result in the case of the small fixing force, the graph 101 shows the result in the case of the middle fixing force, and the graph 102 shows the result in the case of the large fixing force. As can be seen from the figure, the value of the center-of-gravity frequency is largely dispersed depending on hammering positions of the wedge 8. Thus, the case where the center-of-gravity frequency is reversed with respect to the fixing force like the hammering point d5 in the graphs 100, 101 also occurs. For this reason, if the hammering sound in suitable one portion of the wedge 8 is set as a representative value, then, the dispersion becomes large.

Figure 8:
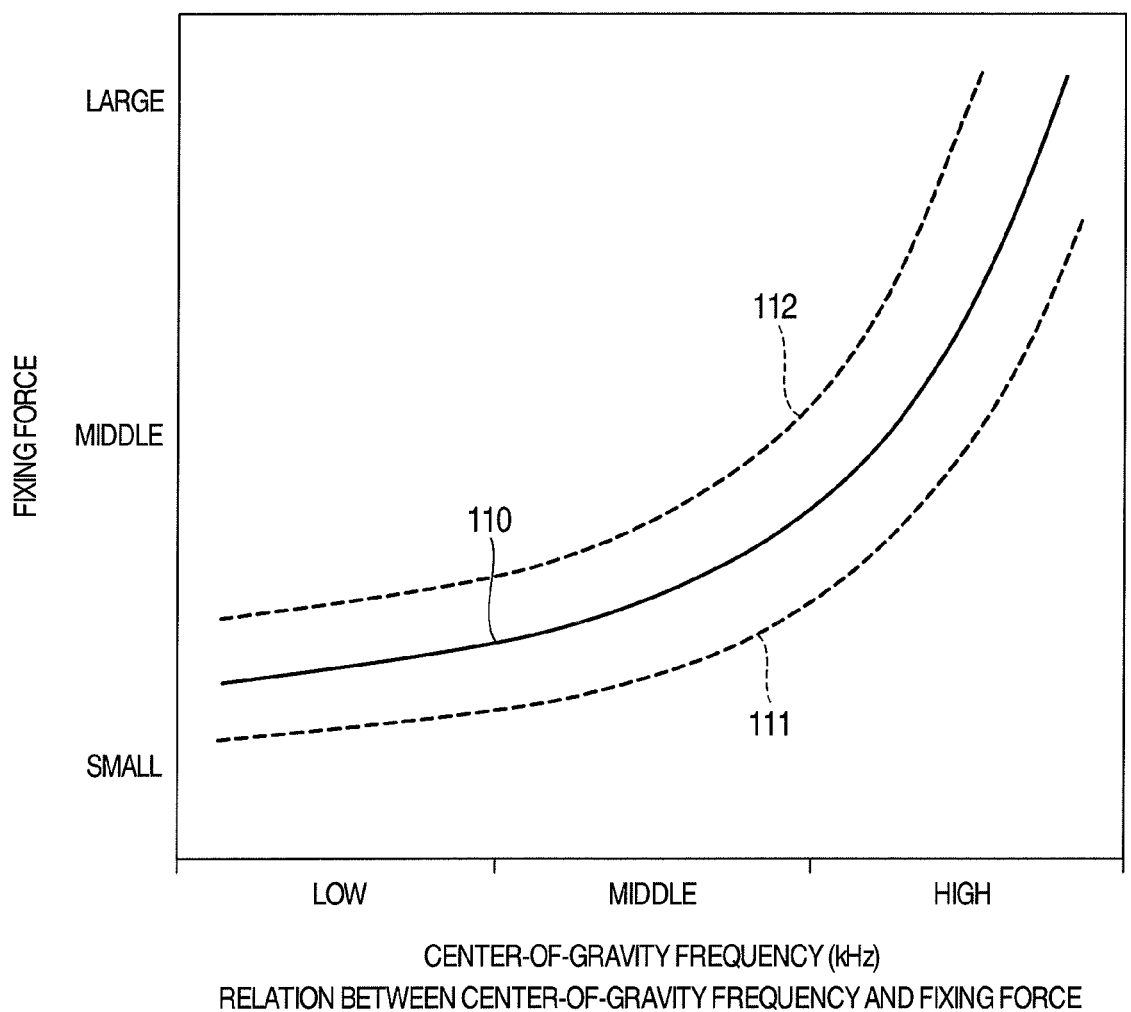
FIG. 8 is a graph representing a relationship between the center-of-gravity frequency and a fixing force.

FIG. 8 shows a relationship between an average value of the center-of-gravity frequencies obtained from the hammering sounds from the five portions d1 to d5 of the wedge 8, and the wedge fixing force. FIG. 8 shows a tendency in which the higher the center-of-gravity frequency is, the larger the fixing force is.

FIG. 8 shows a graph in which an axis of abscissa represents the center-of-gravity frequency and an axis of ordinate represents the fixing force. In FIG. 8, reference numeral 110 designates an average of the center-of-gravity frequencies from the five hammering points, and reference numerals 111, 112 designate an upper limit range and a lower limit range of the data dispersion, respectively.

The result shown in FIG. 8 is the average of the center-of-gravity frequencies from the five hammering points, and shows that averaging the center-of-gravity frequencies from the five hammering points suppresses the dispersion to a certain level of dispersion, thereby making it possible to obtain a correlative relationship between the center-of-gravity frequency and the fixing force.

When no averaging is carried out, the dispersion increases several times in range, so that the correlative relationship becomes weak.

Figure 9:
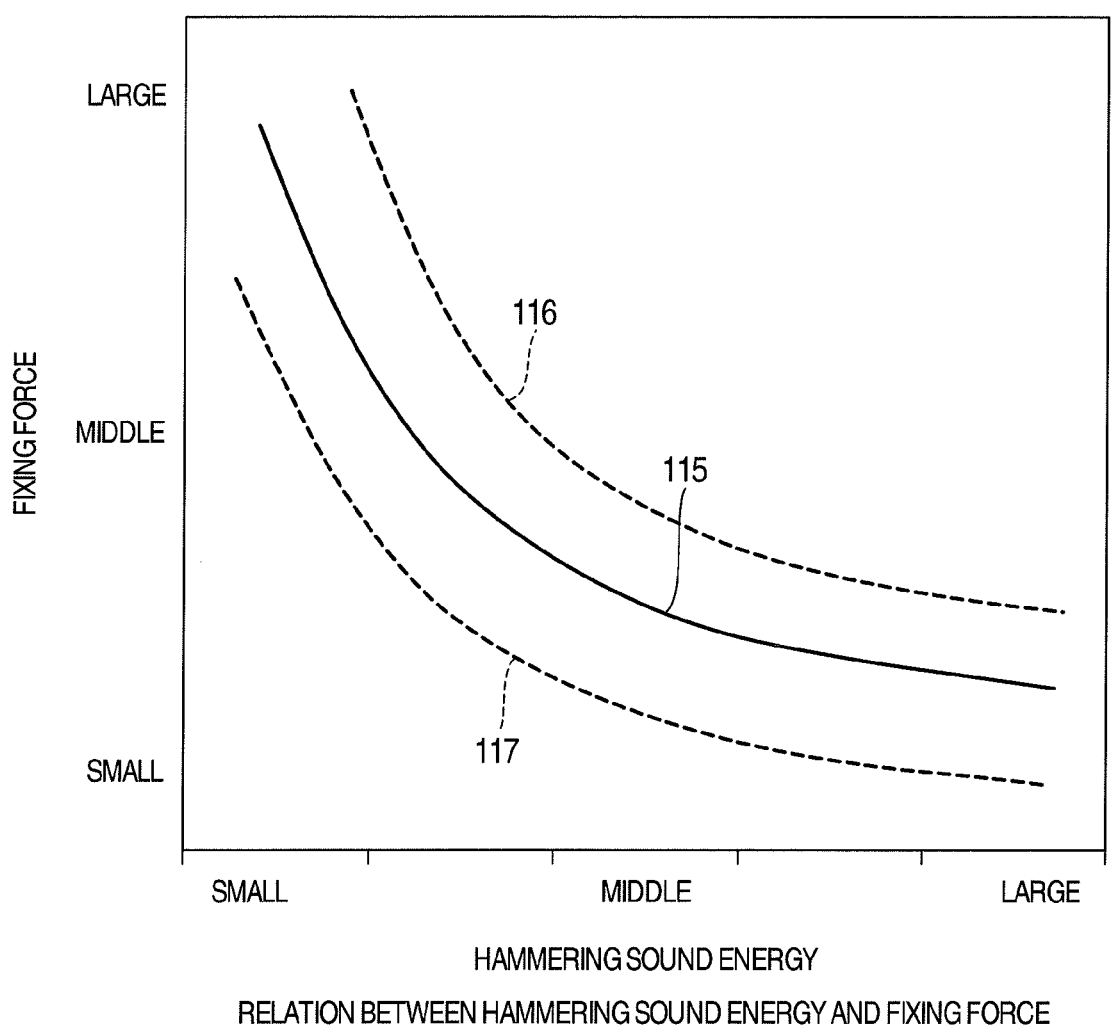
FIG. 9 is a graph representing a relationship between a hammering sound energy and the fixing force.

Similarly, with regard to the hammering sound energy as well defined by Expression (2), the dispersion from the hammering position to the hammering position is large and the averaging makes it possible to reduce the dispersion. FIG. 9 shows a relationship between the hammering sound energy of the average of the hammering sound energies from the five hammering points, and the fixing force. FIG. 9 shows a tendency in which the larger the hammering sound energy is, the smaller the fixing force is.

Expressions used in the averaging of the hammering sound energies from the five hammering points are shown in Expressions (3) and (4), respectively.

In each of Expressions (3) and (4), k represents a number of the hammering sound which is generated when plural portions of one wedge are struck in order, and takes values from 1 to 5.

The average, $\bar{f}_g$, of the center-of-gravity frequencies from the five hammering sounds is expressed by Expression (3):

$$\bar{f}_g = \frac{1}{5}\sum_{k=1}^{k=5}\left(\frac{\int (X_k(\omega) \times \omega)d\omega}{\int X_k(\omega)d\omega}\right) \quad (3)$$

The average, $\bar{E}_s$, of the hammering sound energies from the five hammering points is expressed by Expression (4):

$$\bar{E}_s = \frac{1}{5}\sum_{k=1}^{k=5}\int X_k(\omega)d\omega \quad (4)$$

Further, the dispersions shown in Expressions (4) and (5), respectively, can be obtained from the five hammering sounds.

The dispersion, $f_d$, of the center-of-gravity frequencies from the five hammering sounds is obtained from Expression (5):

$$f_d = \max\left(\frac{\int (X_k(\omega) \times \omega)d\omega}{\int X_k(\omega)d\omega}\right) - \min\left(\frac{\int (X_k(\omega) \times \omega)d\omega}{\int X_k(\omega)d\omega}\right) \quad (5)$$

The dispersion, $E_d$, of the hammering sound energies from the five hammering sounds is obtained from Expression (6):

$$E_d = \max(\int X_k(\omega)d\omega) - \min(\int X_k(\omega)d\omega) \quad (6)$$

Although in the first embodiment, the dispersion is expressed by a difference between a maximum value and a minimum value of the five pieces of data, alternatively, it can also be expressed by any other suitable method such as standard deviation.

Figure 10:
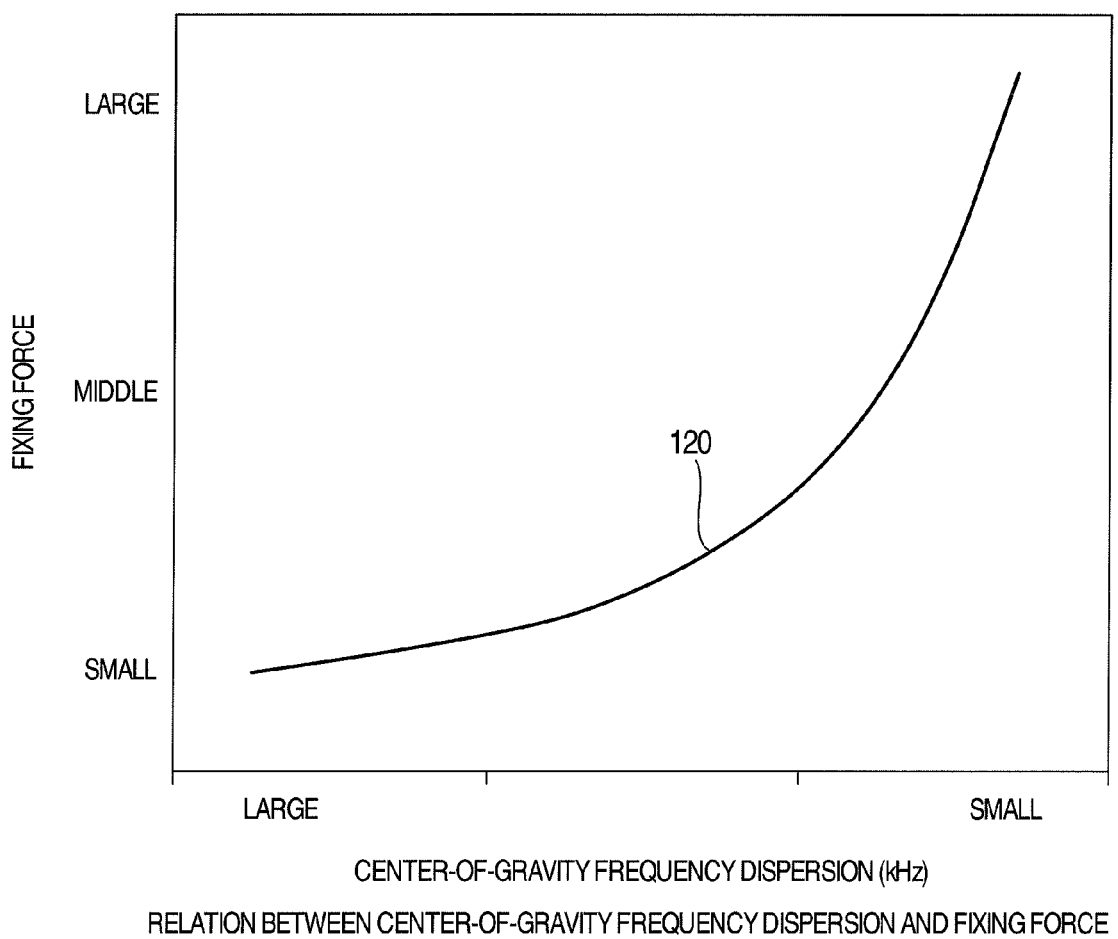
FIG. 10 is a graph representing a relationship between a dispersion of the center-of-gravity frequencies and the fixing force.

In the results of the study until now, the relationship as shown in a graph 120 of FIG. 10 is also obtained between the fixing force and the center-of-gravity frequency. Thus, the results of the study until now show a tendency in which the smaller the fixing force becomes, the larger the dispersion of the center-of-gravity frequencies among the hammering sounds becomes.

Although the relationship between the center-of-gravity frequency and the fixing force which is obtained from Expression (3), and the relationship between the hammering sound energy and the fixing force which is obtained from Expression (4) are as shown in FIGS. 8 and 9, respectively, each of the center-of-gravity frequency and the hammering sound energy has a correlation with the fixing force. Then, when the correlative relationship with the fixing force is expressed based on the two kinds of feature quantities: the center-of-gravity frequency; and the hammering sound energy, the correlative relationship is expressed by a three-dimensional curved surface 130 shown in FIG. 11. As far as the estimation concerned of the fixing force using this three-dimensional curved surface 130, the fixing force is estimated based on a value 133 corresponding to an intersection point, in the plane coordinates, which is expressed by both a value 131 of the center-of-gravity frequency, and a value 132 of the hammering sound energy. In this case, the estimation in which the dispersion is smaller than that in the estimation made from one kind of data becomes possible.

Figure 11:
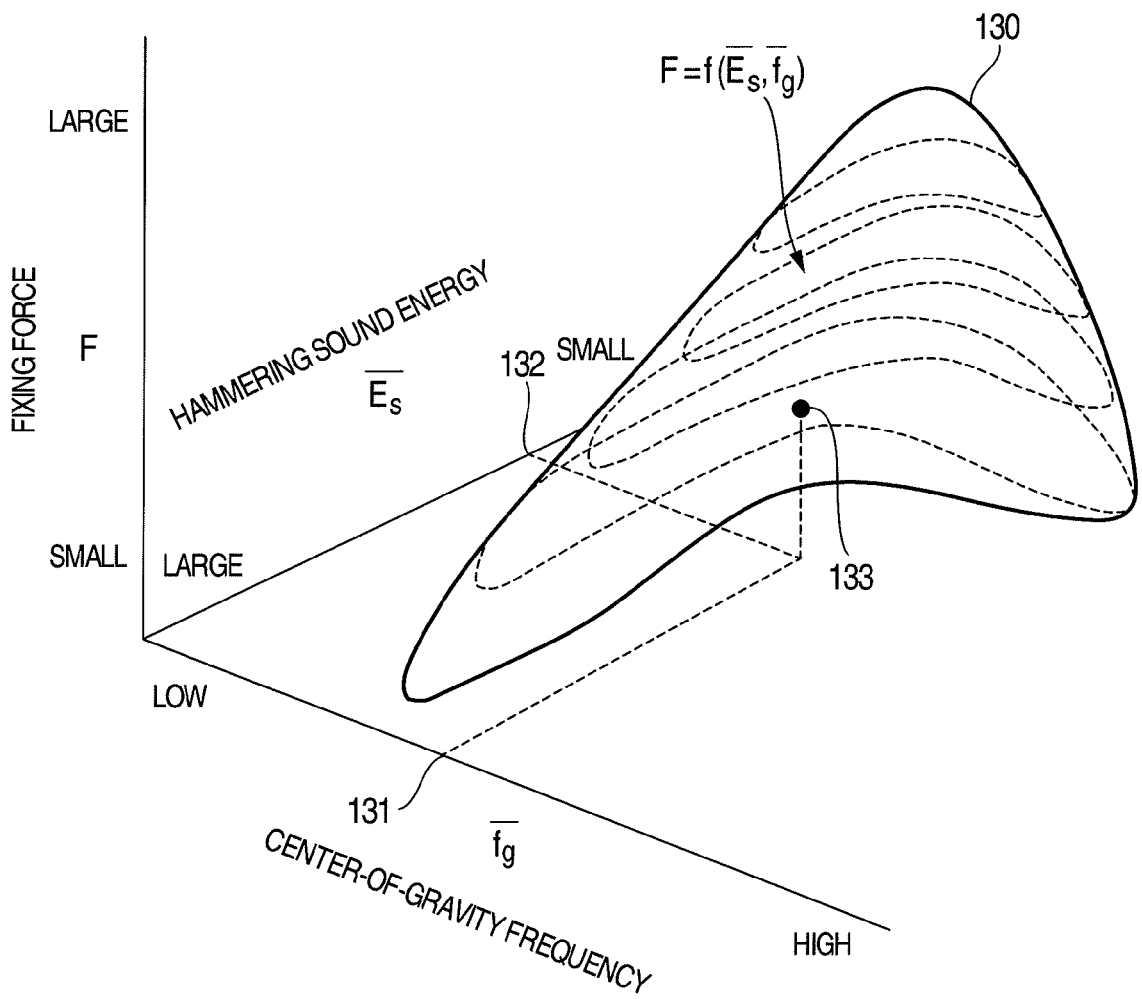
FIG. 11 is a graph representing a relationship among the center-of-gravity frequency, the hammering sound energy, and the fixing force.

A method of concretely obtaining the three-dimensional curved surface shown in FIG. 11 is as follows. For example, coefficients, a1 to a5, are obtained in such a way that a difference between a measured value and an estimate value becomes minimum by using Expression of the quadratic curve of Expression (7), the method of least squares, and the like, thereby making it possible to obtain an estimate curved surface:

$$F = a_1 \times (\bar{f}_g)^2 + a_2 \times (\bar{E}_s)^2 + a_3 \times \bar{f}_g + a_4 \times \bar{E}_s + a_5 \quad (7)$$

where F is the fixing force.

Although in the above case, the estimation expression is expressed by the quadratic curve, alternatively, the estimation expression may also be created by using either a primary expression or a third-order or more higher-order expression.

In addition, although the center-of-gravity frequency and the hammering sound energy are both used as the estimation factors, alternatively, a combination of the center-of-gravity frequency dispersion, $f_d$, and the hammering sound energy dispersion, $E_d$, may also be used as the estimation factor. Moreover, it is also possible to use an estimation expression based on multidimensional data using two or more factors.

In addition, fixing force evaluation examinations which were based on the hammering sounds and which were made by the inventors rarely showed a tendency in which the relationship between the center-of-gravity frequency and the hammering sound energy was reversed in some cases. In such cases, the abnormality of the fixing state(s) of the member(s) is shown in many cases. Therefore, the abnormal fixing state can also be discriminated by utilizing the conflicting results in the data having two kinds of correlations.

Next, a description will be given with respect to a hammering force calibrating method when the hammering force is calibrated in the wedge fixing force measuring apparatus 20.

The calibration is effective in pre-use confirmation, periodic calibration, and reduction of the dispersion of machine differences in plural wedge fixing force measuring apparatuses, and thus is preferably carried out. Moreover, since the hammering sound energy largely receives the influence of the hammering force, when the hammering energy is used as the estimation factor, for the purpose of removing the influence of the variation of the hammering force, the hammering action needs be carried out with the same hammering force on a constant basis.

Figure 12:
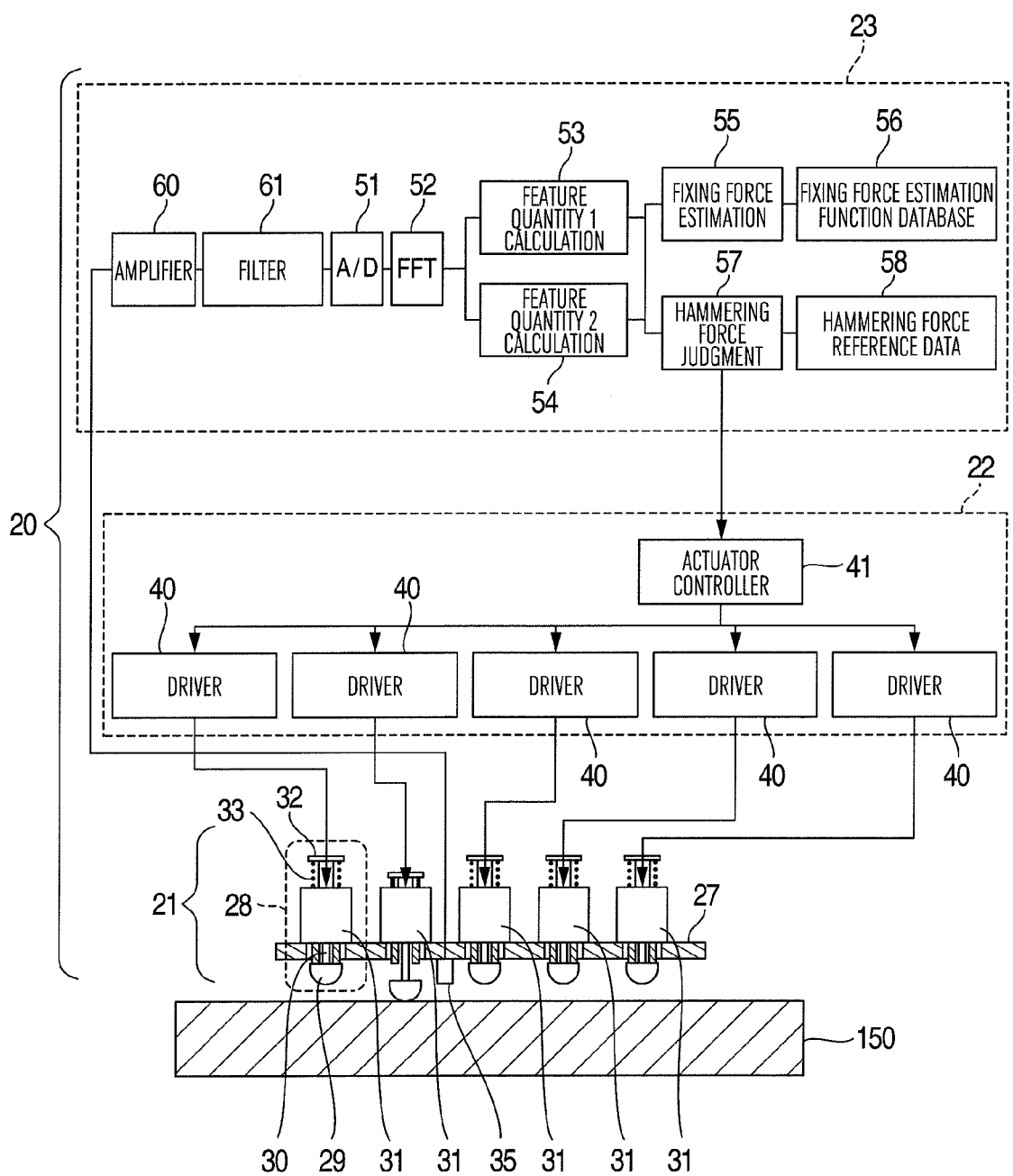
FIG. 12 is an explanatory view of a hammering force (hitting force) calibrating method in the wedge fixing force measuring apparatus according to the first embodiment of the present invention.

In FIG. 12, reference numeral 150 designates a member for calibration of the wedge fixing force measuring apparatus 20.

Firstly, the hammering unit 21 strikes the five portions of the member 150 for calibration, thereby collecting reference hammering sounds. Reference center-of-gravity frequencies, reference hammering sound energies, and the like for the five hammering mechanisms 28 are collected from the reference harming sounds. Also, the data on the reference center-of-gravity frequencies, the reference hammering sound energies, and the like is recorded as hammering force reference master data.

In the calibration, the wedge fixing force measuring apparatus 20 as the object of the calibration is set to the same state as that in a phase of collection of the reference data for the member 50 for calibration. Thus, the hammering sounds from the five hammering mechanisms 28 are controlled. A feature quantity 1 and a feature quantity 2 are calculated from the five hammering sounds thus collected. The center-of-gravity frequency, the hammering sound energy, and the like for the five hammering mechanisms are collected, and are then compared with the hammering force reference data 58 in the hammering force judging unit 57. When the calibration object data falls within the tolerance level with respect to the hammering force reference data 58, the fact that the wedge fixing force measuring apparatus 20 is in the normal state may be displayed for an operator by a display function (not shown).

On the other hand, when the calibration object data deviates from the tolerance level with respect to the hammering force reference data 58, and thus the calibration is required, firstly, the fact that the hammering force is in the abnormal state is displayed for the operator by the display function. In addition, the PWM control conditions of the drive currents for the five hammering mechanisms 28 are changed for the actuator controller 41 in accordance with a signal sent from the hammering force judging unit 57. As a result, the hammering forces are adjusted. In addition, when it is impossible to cope with such a situation only by the change of the PWM control conditions, the measures such as repair are carried out. Moreover, preferably, the results from the hammering force judging unit 57 are recorded as a calibration history in the recorder.

According to the first embodiment of the present invention, the plural kinds of feature quantities having the correlation with the fixing force are obtained from the power spectra of the hammering sounds. Also, for the purpose of estimating the fixing force based on the relationship between the plural kinds of feature quantities, and the fixing force, it is possible to enhance the fixing force estimation precision.

Second Embodiment

A wedge fixing force measuring apparatus according to a second embodiment of the present invention will be described with reference to FIG. 13.

Figure 13:
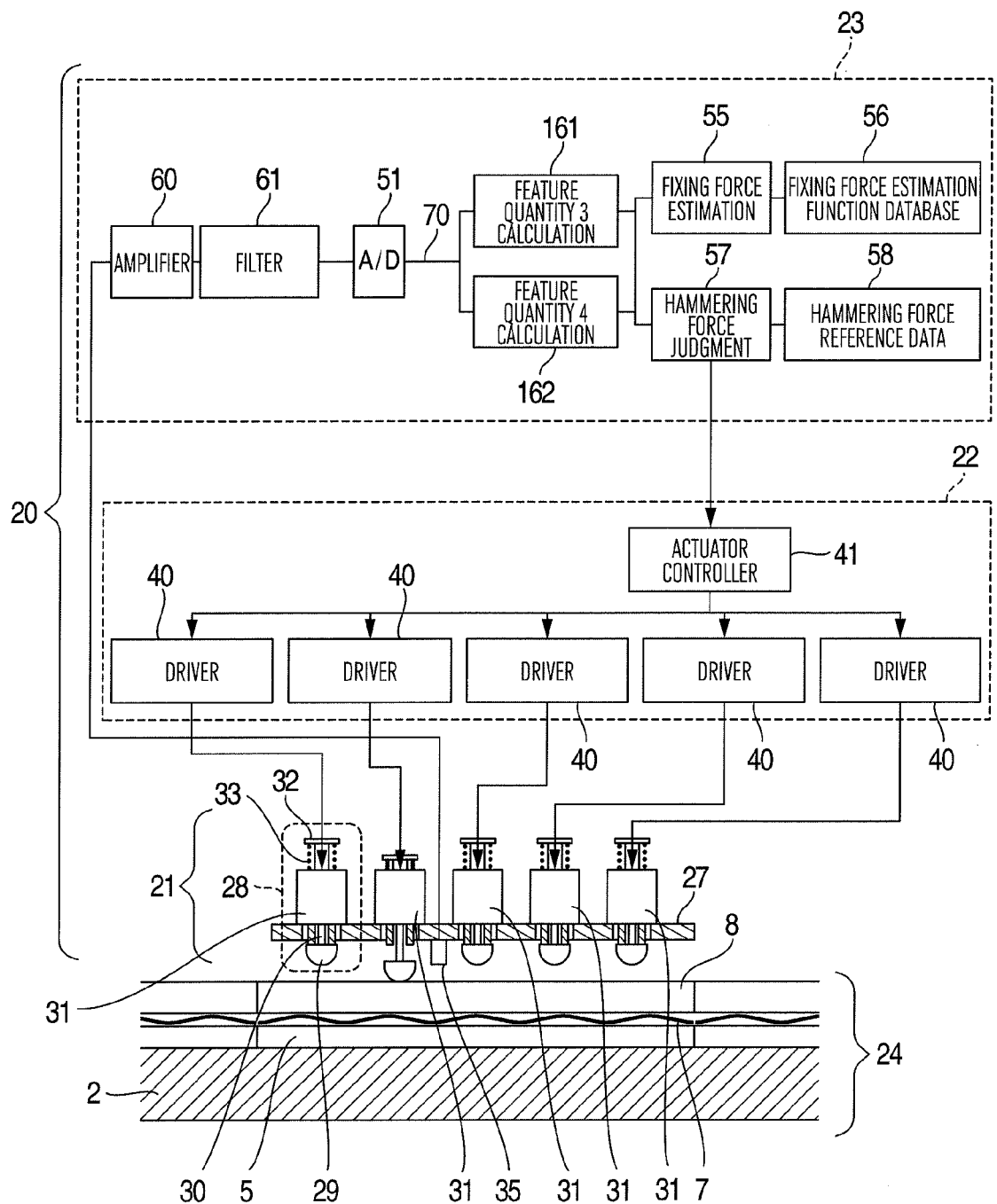
FIG. 13 is a block diagram, partly in view, showing a configuration and a structure of a wedge fixing force measuring apparatus according to a second embodiment of the present invention.

The wedge fixing force measuring apparatus 20 of the second embodiment shown in FIG. 13 is different in configuration from the wedge fixing force measuring apparatus 20 of the first embodiment shown in FIG. 1 in that the FFT processor 52 is removed away, and a feature quantity 3 computer 161 and a feature quantity 4 computer 162 are both provided in a subsequent stage of the A/D converter 51. The feature quantity 3 computer 161 and the feature quantity 4 computer 162 are each a unit for carrying out an arithmetic operation for the result from the A/D converter 51. The output from the A/D converter 51 is the time-series hammering sound data 70 shown in FIG. 4. As far as the feature quantities concerned of that data, it is possible to calculate values as the two pieces of data 165, 166 as the peak data on the intensity, an attenuation rate representing the feature of an envelope 166 of the data, and the like. A wedge fixing force estimating method based on those feature quantities is the same as that in the first embodiment.

There are various materials and fixing methods in the assembly of the electric machine. For example, in those instances where the gutter is generated and thus the assembly fault is caused, the generation of the gutter, and the generation of the peak values 165, 166 show the strong correlation. In the assembly of the elongated member(s), the style of the vibrancy of the sound after the hammering is changed due to the fixing states of the members, the defects or the like in many cases. In such cases, the attenuation rate or the like as the feature of the envelope 166 is largely changed.

According to the second embodiment of the present invention, it is possible to enhance the fixing force estimation precision for the data in which the feature quantity obtained from the time-series hammering sound data 70 obtained from the hammering sounds, and the fixing force show the correlation.

Third Embodiment

Figure 14:
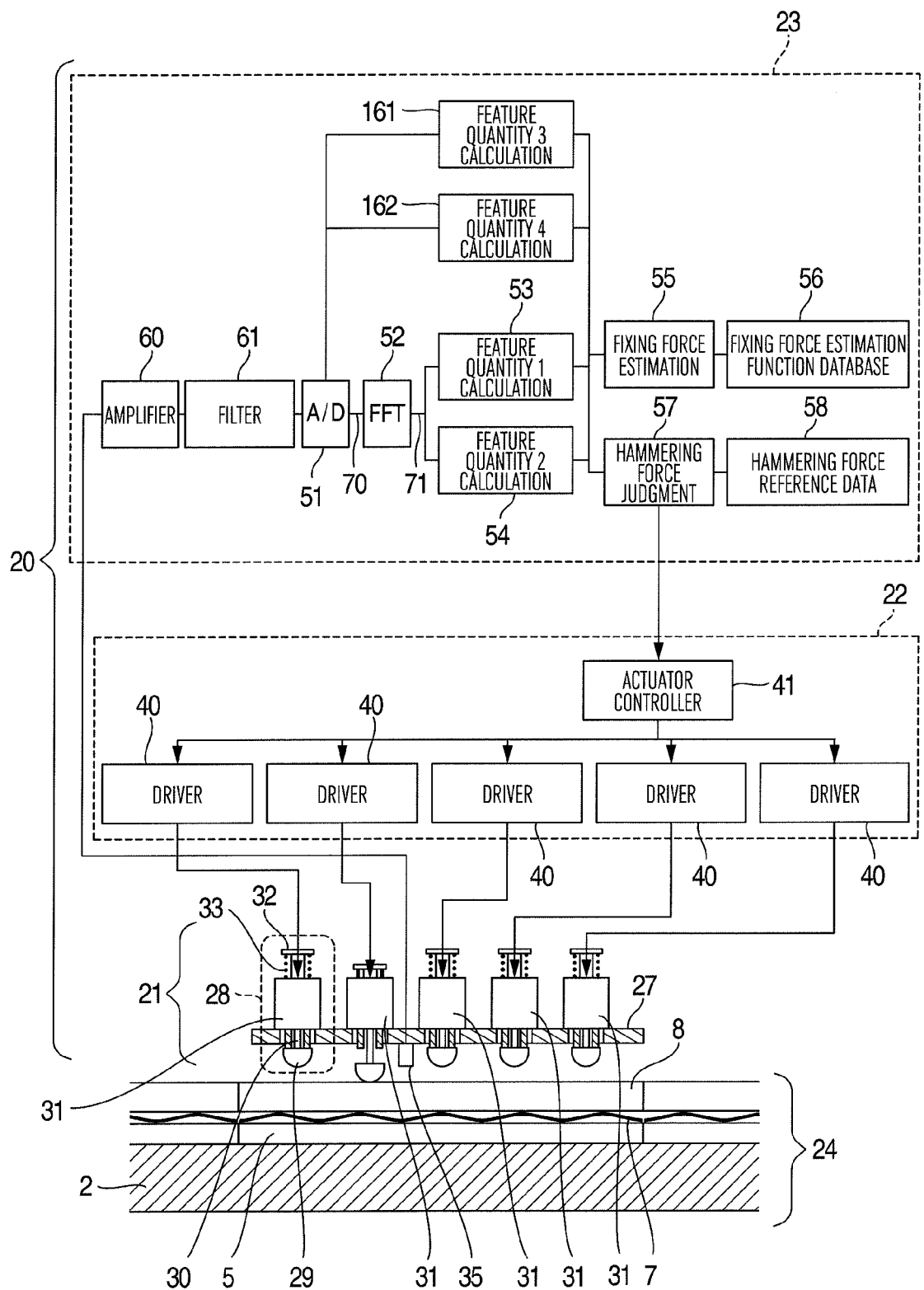
FIG. 14 is a block diagram, partly in view, showing a configuration and a structure of a wedge fixing force measuring apparatus according to a third embodiment of the present invention.

A description will now be given with respect to a wedge fixing force measuring apparatus according to a third embodiment of the present invention with reference to FIG. 14. The wedge fixing force measuring apparatus 20 is described as follows. The various feature quantities showing the correlation with the fixing force are obtained from the power spectrum data 71 as the output from the FFT processor 52 which FFT-processes the time-series hammering sound data 70 as the output from the A/D converter 51. Also, the fixing force is estimated based on a combination of these feature quantities.

According to the third embodiment of the present invention, it is possible to respond to both the kind of factor in which the time-series hammering sound data 70 and the fixing force show the correlation, and the kind of power spectrum data 71 as the frequency data. Therefore, it is possible to estimate the fixing forces for the various fixing states.

The present invention is by no means limited to the above embodiments, and contains various modified changes thereof. For example, the above embodiments have been described in detail for describing the present invention in a simplified manner, and thus are not necessarily limited to ones including all constituent elements described above.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A fixing force measuring apparatus comprising:
hitting means for applying a predetermined controlled hitting force to a surface of a plate-like member to generate a hitting sound;
means for collecting the hitting sound generated;
means for obtaining plural kinds of feature quantities from the hitting sound; and
fixing force estimating means for estimating the fixing force from a database representing a relationship between the plural kinds of feature quantities previously prepared in correspondence to a kind of evaluation object, and the fixing force, and the feature quantities extracted from said database and the hitting sound;
wherein a solenoid type actuator is used as said hitting means for applying the predetermined controlled hitting force to generate the hitting sound, thereby controlling the hitting force by using a PWM system.

2. The fixing force measuring apparatus according to claim 1, further comprising:
means for judging a hitting force from a relationship among a member for calibration for hitting force calibration, plural feature quantities for said member for calibration previously obtained, and the hitting sound, and calibrating the hitting force when the hitting force deviates from a stipulated range.

3. The fixing force measuring apparatus according to claim 1, wherein a value of a center-of-gravity frequency, and a value of a hitting sound energy from an energy of a power spectrum obtained from a power spectrum of the hitting sound collected are used as the feature quantities.

4. The fixing force measuring apparatus according to claim 1, wherein a peak value obtained from a hitting sound waveform as time-series data on the hitting sound collected, and an attenuation rate are used as the feature quantities.

5. The fixing force measuring apparatus according to claim 1, wherein a value of a center-of-gravity frequency, a value of a hitting sound energy from an energy of a power spectrum obtained from a power spectrum of the hitting sound collected, a peak value obtained from, and a hitting sound waveform as time-series data on the hitting sound, and an attenuation rate are used as the feature quantities.

6. A fixing force measuring apparatus, comprising:
hitting means for applying a predetermined controlled hitting force to plural portions of a surface of a plate-like member to generate plural hitting sounds;
means for collecting the plural hitting sounds generated;
means for obtaining plural kinds of feature quantities from the plural hitting sounds collected;
means for averaging the plural feature quantities for every kind of feature quantity, thereby obtaining plural kinds of averaged feature quantities; and
means for obtaining the fixing force so as to correspond to the fixing force corresponding to the plural kinds of averaged feature quantities by using a database representing a correlative relationship between the fixing force of said plate-like member previously obtained, and the plural kinds of averaged feature quantities;
wherein a solenoid type actuator is used as said hitting means for applying the predetermined controlled hitting force to generate the hitting sound, thereby controlling the hitting force by using a PWM system.

7. The fixing force measuring apparatus according to claim 6, further comprising:
means for judging a hitting force from a relationship among a member for calibration for hitting force calibration, plural feature quantities for said member for calibration previously obtained, and the hitting sound, and calibrating the hitting force when the hitting force deviates from a stipulated range.

8. The fixing force measuring apparatus according to claim 6, wherein a value of a center-of-gravity frequency, and a value of a hitting sound energy from an energy of a power spectrum obtained from a power spectrum of the hitting sound collected are used as the feature quantities.

9. The fixing force measuring apparatus according to claim 6, wherein a peak value obtained from a hitting sound waveform as time-series data on the hitting sound collected, and an attenuation rate are used as the feature quantities.

10. The fixing force measuring apparatus according to claim 6, wherein a value of a center-of-gravity frequency, a value of a hitting sound energy from an energy of a power spectrum obtained from a power spectrum of the hitting sound collected, a peak value obtained from, and a hitting sound waveform as time-series data on the hitting sound, and an attenuation rate are used as the feature quantities.

11. A method of measuring a fixing force, comprising:
applying a predetermined controlled hitting force to a surface of a plate-like member to generate a hitting sound;
collecting the hitting sound generated;
obtaining plural kinds of feature quantities from the hitting sound; and
estimating the fixing force from a database representing a relationship between the plural kinds of feature quantities previously prepared in correspondence to a kind of evaluation object, and the fixing force, and the feature quantities extracted from said database and the hitting sound;
wherein a solenoid type actuator is used for applying the predetermined controlled hitting force to generate the hitting sound, thereby controlling the hitting force by using a PWM system.

12. A method of measuring a fixing force, comprising:
applying a predetermined controlled hitting force to plural portions of a surface of a plate-like member to generate plural hitting sounds;
collecting the plural hitting sounds generated;
obtaining plural kinds of feature quantities from the plural hitting sounds collected;
averaging the plural feature quantities for every kind of feature quantity, thereby obtaining plural kinds of averaged feature quantities; and
obtaining the fixing force so as to correspond to the fixing force corresponding to the plural kinds of averaged feature quantities by using a database representing a correlative relationship between the fixing force of said plate-like member previously obtained, and the plural kinds of averaged feature quantities;
wherein a solenoid type actuator is used for applying the predetermined controlled hitting force, thereby controlling the hitting force by using a PWM system.

* * * * *